United States Patent
Schmidt

(10) Patent No.: US 10,456,411 B2
(45) Date of Patent: *Oct. 29, 2019

(54) COMPOSITION COMPRISING KETONE BODY AND NICOTINAMIDE ADENINE DINUCLEOTIDE MODULATOR AND METHYL DONOR

(71) Applicant: Tecton Group, LLC, Memphis, TN (US)

(72) Inventor: Michael A. Schmidt, Fort Collins, CO (US)

(73) Assignee: Tecton Group, LLC, Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/437,773

(22) Filed: Jun. 11, 2019

(65) Prior Publication Data

US 2019/0290666 A1    Sep. 26, 2019

Related U.S. Application Data

(63) Continuation of application No. 15/456,407, filed on Mar. 10, 2017.

(51) Int. Cl.
| | |
|---|---|
| *A61K 31/683* | (2006.01) |
| *A61K 31/6615* | (2006.01) |
| *A61K 31/19* | (2006.01) |
| *A61K 31/22* | (2006.01) |
| *A61K 45/06* | (2006.01) |

(52) U.S. Cl.
CPC ............ *A61K 31/683* (2013.01); *A61K 31/19* (2013.01); *A61K 31/22* (2013.01); *A61K 31/6615* (2013.01); *A61K 45/06* (2013.01)

(58) Field of Classification Search
CPC .................................................. A61K 31/683
See application file for complete search history.

(56) References Cited

PUBLICATIONS

Newman et al., β-hydroxybutyrate: Much more than a metabolite, Diabetes Research and Clinical Practice, vol. 106, Issue 2, Nov. 2014, pp. 173-181 ("Newman").*
Bough et al., Anticonvulsant Mechanisms of the Ketogenic Diet, Epilepsia, 48(1): 433-58, 2007.*
White et al., Clinical review: Ketones and brain injury, Critical Care, 2011, 15:219.*

* cited by examiner

*Primary Examiner* — Svetlana M Ivanova
(74) *Attorney, Agent, or Firm* — Wilson Sonsini Goodrich & Rosati

(57) ABSTRACT

The present invention provides a composition comprising a mixture of an exogenous ketone body, an exogenous NAD modulator and a methyl donor. Typically, exogenous NAD modulator is an exogenous nicotinamide adenine dinucleotide (NAD) precursor. The present invention also provides a method of using such a composition for treating various clinical conditions, including metabolic disorders and neurocognitive impairments. The compositions of the invention can also be used to improve human performance in various competitive or environmental conditions.

25 Claims, No Drawings

COMPOSITION COMPRISING KETONE BODY AND NICOTINAMIDE ADENINE DINUCLEOTIDE MODULATOR AND METHYL DONOR

FIELD OF THE INVENTION

The present invention relates to a composition comprising a mixture of an exogenous ketone body ("EK"), an exogenous nicotinamide adenine dinucleotide ("NAD") modulator and a methyl donor. Typically, exogenous NAD modulator is an exogenous nicotinamide adenine dinucleotide (NAD) precursor. The present invention also relates to a method of using such a composition for treating various clinical conditions, including metabolic disorders and neurocognitive impairments. The present invention further relates to a method of improving human performance in various competitive or environmental conditions.

BACKGROUND OF THE INVENTION

Ketosis is a metabolic state in which some of the body's energy supply comes from ketone bodies (e.g., acetone, acetoacetate and (3-hydroxybutyrate) in the blood. It is characterized by raised level of ketone bodies. Typically, serum concentration of ketone bodies is over 0.5 mM in ketosis. Ketosis is pathological in certain conditions, such as diabetes. However, ketosis can also be achieved using a diet that is very low in carbohydrates, through prolonged fasting, or in intermittent fasting.

A number of clinical conditions can benefit from dietary ketosis, such as epilepsy and other neurological conditions. There is also a growing body of evidence that athletic performance can benefit from ketosis induced by diet. This state of dietary ketosis is attainable, but the ketogenic diets needed to achieve and/or to maintain ketosis are very difficult to sustain. Thus, a source of safe and biologically active exogenous ketone bodies may provide a solution for those seeking to achieve the metabolic state of ketosis, but who cannot or will not follow the necessary restrictive diet to achieve ketosis.

A small number of ketone bodies have been developed for oral delivery, such as the salts of acetoacetate and β-hydroxybutyrate. However, these ketone bodies have largely suffered from poor oral tolerance and side effects. Some are unacceptably high in sodium, which significantly offsets any beneficial effects.

Ketosis is facilitated by nicotinamide adenine dinucleotide ("NAD") modulator, which facilitates the conversion of other ketone bodies (e.g., BHB) to acetoacetate, which is one of the principal steps required for conversion of the ketone bodies to a usable fuel (ultimately as acetyl-CoA). Regarding NAD upregulation, variants of the B vitamin analogue, nicotinamide riboside ("NR"), have been explored for their effects on NAD. NR raises blood and tissue NAD levels far above that of other B vitamin analogues (niacin, nicotinamide, nicotinic acid, nicotinamide mononucleotide).

Upregulation of NAD utilizes methyl donor. Therefore, the amount of available methyl donor is expected to be reduced significantly due to increase in NAD production resulting from administration of exogenous NAD modulator. This depletion in methyl donor can result in various undesired side-effects.

To date, efforts to provide supplementary ketone bodies resulted in poor tolerability of the exogenous ketone body (EK) supplement. Furthermore, all current EK supplements lack NAD modulator, which facilitates the conversion of other ketone bodies to acetoacetate. In addition, conventional supplements directed to upregulating NAD lacks methyl donor to offset the effects of methyl donor depletion.

Therefore, there is a need for a composition that can allow one to achieve the metabolic state of ketosis without the need for a strict diet regime. Furthermore, there is a need for a composition that includes an EK supplement, an NAD modulator and a methyl donor.

SUMMARY OF THE INVENTION

The present invention provides a composition that includes an exogenous ketone body ("EK"), an exogenous NAD modulator and a methyl donor. In some embodiments, the exogenous ketone body comprises an ester of (R)-3-hydroxybutyrate, a derivative of an R-butyrate, a conjugate of butyrate, or a derivative thereof or a combination thereof. Exemplary derivatives of beta-hydroxybutyrate ("BHB") include esters of BHB, and compounds where the hydroxyl group of BHB is bonded to a group that may be cleaved in vivo to regenerate the free hydroxyl group, such as acetate, formate, benzoates and carbamates. Yet in other embodiments, the exogenous NAD modulator is an exogenous NAD precursor, which is converted in vivo to an NAD modulator. Exemplary NAD modulators include, but are not limited to, nicotinoyl riboside, nicotinamide riboside, nicotinic acid mononucleotide, nicotinamide mononucleotide or a derivative thereof (such as β-nicotinamide ribose monophosphate), or a combination thereof.

The composition of the invention also includes a methyl donor. In one particular embodiment, the methyl donor comprises vitamin $B_{12}$, folate, S-adenosylmethionine, betaine, choline, or a combination thereof.

Another aspect of the invention provides a method for treating a subject suffering from a clinical condition associated with an elevated plasma level of free fatty acids. The method comprises administering to the subject a therapeutically effective amount of a composition of the invention.

Yet another aspect of the invention provides a method for suppressing appetite, treating obesity, promoting weight loss, maintaining a healthy weight or decreasing the ratio of fat to lean muscle in a subject. The method comprises administering to the subject in need thereof a therapeutically effective amount of a composition of the invention.

Still another aspects of the invention provide a method for treating a condition selected from muscle impairment and muscle fatigue. The method comprises administering to a subject in need thereof a therapeutically effective amount of a composition of the invention.

Further aspect of the invention provides a method for treating traumatic injury to the brain, including but not limited to traumatic brain injury due to blast. The method comprises administering to a subject in need thereof a therapeutically effective amount of a composition of the invention. In some embodiments, the traumatic brain injury comprises a vascular injury to the brain. Exemplary vascular injuries to the brain include stroke and ischemia.

Another aspect of the invention provides a method for improving neurocognitive function in a subject. The method comprises administering to a subject in need of such a treatment a therapeutically effective amount of a composition of the invention. In one particular embodiment, the method is used to treat a subject suffering from a mild cognitive impairment or Alzheimer's disease.

DETAILED DESCRIPTION OF THE INVENTION

Ketone bodies are chemical compounds that are produced by the liver from fatty acids released from adipose tissue.

Ketone bodies themselves can be used as a source of energy in most tissues of the body. The intake of compounds that boost the levels of ketone bodies in the blood can lead to various clinical benefits, including an enhancement of physical and cognitive performance, and in the treatment of cardiovascular conditions, diabetes, neurodegenerative diseases and epilepsy.

Organs like the brain are fully capable of converting ketone bodies to ATP. For example, for β-hydroxybutyrate ("BHB"), conversion to useful energy includes the steps of converting BHB to acetoacetate, acetoacetate to acetoacetyl CoA, and acetoacetyl CoA to acetyl CoA. Indeed, the amounts and activities of ketone body-metabolizing enzymes in organs such as the brain are not changed by glucose status and always exceed the amount necessary to supply the brain's total energy needs.

Ketone bodies include (R)-3-hydroxybutyrate and acetoacetate. These compounds could in theory be administered directly to achieve elevated levels of ketone bodies in a subject. However, direct administration of the compounds in high doses is unpractical and potentially dangerous. For example, direct administration of either (R)-3-hydroxybutyrate or acetoacetate in high doses of its free acid form can result in significant ketoacidosis following rapid absorption from the gastrointestinal tract. Administration of the sodium salt of these compounds in unregulated amounts is also unsuitable, due to a potentially dangerous sodium overload that could accompany administration of therapeutically relevant amounts of the compounds.

Nicotinamide adenine dinucleotide (NAD+) is a natural coenzyme that functions as an intermediary in cellular oxidation and reduction reactions, as well as an ADP-ribosyltransferase substrate. Altering intracellular NAD+ levels can improve the health of a cell, but introduction of compounds that enter NAD+ metabolic pathways can also prove toxic to cells (e.g., benzamide riboside (BAR)).

In some embodiments, compositions of the invention are capable of improving the health of damaged or diseased cells, for example, by altering intracellular NAD+, NADH, NADP+ or NADPH levels. Moreover, compositions of the invention do not have any significant adverse effects when administered therapeutically, i.e., side-effects are observed in less than 10%, typically less than 5% and often less than 1% of the subject or patient.

In one particular embodiment, the composition of the invention includes an exogenous ketone body ("EK"), an exogenous NAD modulator and a methyl donor. In one embodiment, the compositions of the invention are formulated as a single unit. Thus, the exogenous ketone body, the exogenous NAD modulator and the methyl donor are intimately mixed in one single solid or liquid solution. Suitable exogenous ketone bodies include an ester of β-hydroxybutyric acid, in particular an ester of (R)-3-hydroxybutyrate of the formula:

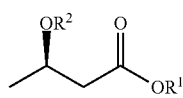

I where $R^1$ is alkyl, hydroxyl alkyl, or a linker attached to a phospholipid, and $R^2$ is hydrogen, carboxylate (e.g., acetate, formate, benzoates and carbamates) or alkyl. Alkyl refers to a saturated linear monovalent hydrocarbon moiety of one to twelve, typically one to eight, and often two to six, carbon atoms or a saturated branched monovalent hydrocarbon moiety of three to twelve, typically three to six, carbon atoms. Exemplary alkyl groups include, but are not limited to, methyl, ethyl, n-propyl, 2-propyl, tert-butyl, pentyl, and the like. The term "hydroxyl alkyl" refers to alkyl group having one or more, typically one, two or three hydroxyl (—OH) functional groups. Exemplary hydroxyl alkyl groups include 3-hydroxylbutyl, 2-hydroxylbutyl, 1-methyl-2-hydroxylpropyl, 1,3-butanediol, glycerol, glycol, etc. In one particular embodiment, $R^1$ is (R)-3-hydroxylbutyl. Still in another embodiment, $R^2$ is hydrogen. Yet in another embodiment, EK is glycerol esters of hydroxybutyric acid, such as those disclosed in U.S. Pat. No. 5,693,850, issued to Birkhahn et al., which is incorporated herein by reference in its entirety. In particular, the glycerol can include one, two or three BHB's.

In one particular embodiment, EK is glycerol ester of BHB of the following formula:

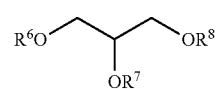

G-1 where each of $R^6$, $R^7$ and $R^8$ is independently selected from the group consisting of hydrogen or BHB moiety of the formula —C(=O)CH$_2$CH(OR$^2$)CH$_3$ (where $R^2$ is H or a hydroxyl protecting group) or a hydroxyl protecting group; provided at least one of $R^6$, $R^7$ and $R^8$ is BHB moiety. Suitable hydroxyl protecting groups includes hydroxyl protecting group as discussed herein for $R^2$, as well as those known to one skilled in the art of organic chemistry. See, for example, T. W. Greene and P. G. M. Wuts, *Protective Groups in Organic Synthesis*, 3$^{rd}$ edition, John Wiley & Sons, New York, 1999; Harrison and Harrison et al., *Compendium of Synthetic Organic Methods*, Vols. 1-8 (John Wiley and Sons, 1971-1996; chem.iitb.ac.in/~kpk/pg.pdf; and faculty.chemistry.harvard.edu/files/myers/files/7-protective_groups_.pdf, all of which are incorporated herein by reference in their entirety. In some embodiments, hydroxyl protecting group is an acyl group, in particular and acetyl group.

The amount of exogenous ketone body present in the composition of the invention can range from about 1 mg to about 50,000 mg, typically from about 10,000 mg to about 25,000 mg, and often from about 15,000 mg to about 20,000 mg. The term "about" when referring to a numeric value means±20%, typically ±10% and often ±5% of the numeric value.

One particular aspect of the invention provides a composition where the EK (e.g., BHB or a derivative thereof or a combination thereof) is bound to a phospholipid, and methods for using and producing the same. In one particular embodiment, the EK is bound to a phospholipid that comprises a fatty acid ester moiety that is derived from a substantially non-immunogenic $C_4$-$C_{22}$ fatty acid. In some embodiments, the $C_4$-$C_{22}$ fatty acid is an omega-3 fatty acid, an omega-6 fatty acid, an omega-9 fatty acid or a polyunsaturated fatty acid ("PUFA"). Exemplary fatty acids that are useful in the invention include, but are not limited to, docosahexaenoic acid (DHA), eicosapentaenoic acid (EPA), stearidonic acid (SDA), α-linolenic acid (ALA), eicosatetraenoic acid (ETA), γ-linolenic acid (GLA), dihomo-γ-linolenic acid (DGLA), calendic acid (CLA), and docosapentaenoic acid (DPA).

Still in other embodiments, the phospholipid further comprises choline, serine, inositol, ethanolamine, or other polar group. The phospholipids can be derived from yeast, marine animal (such as krill), plant (such as sunflower seed), and/or marine plant (such as microalgae). The phospholipids can also be synthetically modified (e.g., catalytically re-randomized), e.g., via esterfication/transesterfication/acylation. Such synthetic modifications (e.g., re-randomization) can be used to prepare phospholipids comprising a wide variety of different fatty acid esters and/or a wide variety of combination of fatty acid esters. Furthermore, such synthetic modification also provides a wide variety of polar groups to be attached to the phosphate moiety of the phospholipid. Such synthetic modification can be achieved using an enzyme, a chemical catalyst, ultrasound, electromagnetic energy, or a combination thereof. In some embodiments, synthetic modification comprises reacting phospholipids with fatty acids, to modify (e.g., rearrange) one or more of the terminal positions associated with the phospholipid, removing or hydrolyzing at least one fatty acid ester group to produce the hydroxyl group, and covalently attaching (i.e., forming an ester group with) at least one specific fatty acid of $C_4$ or higher, e.g. $C_{16}$, $C_{18}$, $C_{20}$, or $C_{22}$, to produce the fatty acid ester group.

Still other aspects of the invention provide liposome compositions comprising a structured lipid. In some embodiments, the structured lipid comprises a phospholipid including, but not limited to, compound of formula PL-1 discussed below. Still in other embodiments, the structured lipid comprises a first fatty acid ester in which the first fatty acid is derived from a first lipid source, a second fatty acid ester in which the second fatty acid is derived from a second lipid source, and a third fatty acid ester in which the third fatty acid is derived from a third lipid source. In some particular embodiments, the second fatty acid is EPA and the third fatty acid is DHA. Still in other particular embodiments, the second fatty acid is ETA. Yet in other particular embodiments, the second fatty acid is ETA, EPA, or DHA.

In one particular embodiment of the invention, the phospholipid is of the formula:

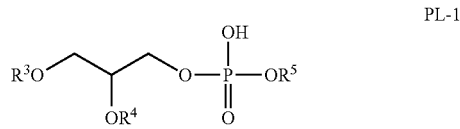

PL-1 where at least one of $R^3$ and $R^4$ is BHB or a derivative thereof (i.e., $CH_3$—$CH(OR^2)$—$CH_2$—$C(=O)$—, where $R^2$ is as defined herein), and the other is a $C_4$-$C_{22}$ fatty acid moiety (i.e., —$C(=O)C_3$-$C_{21}$ fatty acid); and $R^5$ together with the oxygen atom to which it is attached forms choline, serine, inositol, or ethanolamine moiety. In one particular embodiment, $R^3$ is BHB or a derivative thereof and $R^4$ is $C_4$-$C_{22}$ fatty acid. Yet in another embodiment $R^3$ is $C_4$-$C_{22}$ fatty acid and $R^4$ is BHB or a derivative thereof. Still in another embodiment, both $R^3$ and $R^4$ are BHB or a derivative thereof, each of which is independent of the other (i.e., $R^2$ in $R^3$ can be H and $R^2$ in $R^4$ can be acetate, etc.). Suitably fatty acids for $R^3$ or $R^4$ include those described herein such as DHA, EPA, SDA, ALA, ETA, DPA, GLA, DGLA, and CLA.

In another embodiment, the $C_4$-$C_{22}$ fatty acid is an omega-3 fatty acid, an omega-6 fatty acid, or an omega-9 fatty acid.

Still in another embodiment, the $C_4$-$C_{22}$ fatty acid comprises α-linolenic acid (ALA), docosahexaenoic acid (DHA), eicosatetraenoic acid (ETA), eicosapentaenoic acid (EPA), stearidonic acid (SDA), α-linolenic acid (GLA), calendic acid (CLA), docosapentaenoic acid (DPA), or a combination thereof.

Yet in other embodiments, the fatty acid is a $C_{16}$-$C_{22}$ fatty acid such as DHA, EPA, ETA, or a combination thereof.

Exemplary exogenous NAD modulators that are useful in compositions of the invention include, but are not limited to, nicotinamide riboside halide or derivatives (collectively or individually sometimes referred to as "NR"), where halide can be iodide, bromide or chloride. Typically, halide is chloride. Nicotinamide riboside chloride has been shown in animals and in humans to raise blood and tissue levels of NAD. Thus, NR represents an exogenous precursor to endogenous NAD formation. It is known that the conversion of β-hydroxybutyrate to acetoacetate is NAD-dependent. Compositions of the invention combine exogenous ketone body (such as BHB) and NAD modulator into a single unit. In some embodiments, NAD modulator is NR. Particularly useful NAD modulators include nicotinamide riboside, nicotinamide riboside chloride, nicotinamide mononucleotide or a combination thereof.

The term "derivatives" when referring to nicotinamide riboside refers to compounds in which one or more of the hydroxyl groups are protected with a protecting group and can be cleaved in vivo to produce free hydroxyl group. Exemplary protecting groups include acetyl group ($CH_3C(=O)$—), acetoacetyl group, formate, benzoates, carbamates, etc.

The amount of exogenous NAD modulator present in the composition of the invention can range from about 0.001 mg to about 5,000 mg, typically from about 250 mg to about 1000 mg, and often from about 125 mg to about 2000 mg.

Generally, the ratio between the exogenous ketone body and the exogenous NAD modulator in the composition of the invention ranges from about 50,000,000:1 to about 10:1, typically from about 100:1 to about 25:1 and often from about 160:1 to about 10:1.

Compositions of the invention not only raise blood ketone bodies by providing an exogenous ketone body, but also include exogenous NAD modulator that facilitates or aid in conversion of ketone bodies to acetoacetate. When administered, the exogenous ketone body BHB is converted to acetoacetate in vivo via the enzyme BHB dehydrogenase, which is modulated by the exogenous NAD modulator. BHB dehydrogenase is NAD-dependent. Thus, the exogenous NAD modulator upregulates endogenous NAD synthesis, which accelerates the conversion of BHB to acetoacetate. In this manner, more acetoacetate is readily available to be converted to acetyl-Co-A for direct use as an energy substrate.

This combination of active agents (EK and NAD modulator) is applicable across a range of work and performance states where greater energy from a non-lipid and non-carbohydrate substrate is desired. This combination of active agents is also applicable across a range of clinical conditions where greater energy from a non-lipid and non-carbohydrate substrate is desired, where NAD production is low, where greater NAD demands exist, or where NAD is being consumed by other physiologic processes (such as PARP-1 activation).

Compositions of the invention are useful in elevating blood concentrations of ketone bodies when administered to a subject, as well as increasing blood and tissue levels of NAD. By using exogenous NAD modulator (e.g., NR) to raise NAD to facilitate conversion of exogenous ketone bodies to acetoacetate, it is believed that exogenous NAD modulator use is accompanied by elevated plasma methylnicotinamide (methylated nicotinamide), increased methylnicotinamide excretion in urine, elevated nuclear uracil, and elevated serum, plasma, or whole blood homocysteine. Typically, the methyl groups needed to form methylnicotinamide are derived from a small pool of endogenous methyl donors. The amount of available methyl donor is expected to be reduced significantly due to increase in NAD production resulting from administration of exogenous NAD modulator and the resultant methylation of nicotinamide. Thus, compositions of the invention also include an exogenous methyl donor. Exemplary exogenous methyl donor that can be used in compositions of the invention include, but are not limited to, vitamin $B_{12}$, folate, betaine, choline, or a derivative thereof or a combination thereof. Without being bound by any theory, it is believed that inclusion of exogenous methyl donor in compositions of the invention allows maintaining of the endogenous methyl donor pool and/or prevention of methyl pool depletion.

Compositions of the invention are useful in elevating blood concentrations of ketone bodies when administered to a subject, as well as increasing blood and tissue levels of NAD. By using exogenous NAD modulator to raise NAD to facilitate conversion of exogenous ketone bodies to acetoacetate, it is believed that exogenous NAD modulator use is accompanied by inhibition of histone deacetylases (HDAC).

Normally, the tails of histone proteins are positively charged, due to their lysine and arginine residues. These positive charges allow them to interact with the negative charges on the deoxyribonucleic acid (DNA) backbone. When DNA and histones are bound together, the DNA-dependent RNA polymerase (DdRP) cannot make contact with the DNA. This contact inhibition reduces or prevents transcribing of the code inside the DNA, thereby reducing or preventing production of messenger RNA, and ultimately results in reduction or prevention of protein translation.

Acetylation of histone (i.e., covalent attachment of acetyl groups to the lysine and arginine residues) eliminates the positive charges on lysine and arginine and reduces histone-DNA binding. This acetylation of histone results in the DNA to unwind from the histone protein complexes and makes DNA available for transcription. This acetyl addition process is catalyzed by histone acetyltransferases (HATs). Reduced HAT activity correlates with lower global acetylation and transcriptional dysfunction in multiple diseases. Histone deacetylases (HDACs) are a class of protein that catalyze the removal of the acetyl groups from inter alia histone, allowing for DNA to once again interact with histone complexes, and prevent transcription. Thus, HDACs play an important role in the regulation of gene transcription. Histone deacetylate inhibitors (HDIs) have been widely used in psychiatric care and are potentially useful in treating a large number of other disease states, such as neurodegenerative diseases, diabetes, and cancer.

Aberrant hypermethylation is believed to be one of the major mechanisms in carcinogenesis and some critical growth regulatory genes have shown commonality in methylation across solid tumors. Compositions of the invention are useful in epigenetic modification via NR reducing gene promoter methylation and the ketone component blocking histone deacetylase (HDAC). Exogenous ketone bodies such as BHB are HDAC inhibitors. Studies have shown nicotinamide adenine dinucleotide ("NAD") regulates gene methylation. Therefore, compositions of the invention are also useful in clinical conditions associated with disordered gene methylation and acetylation of histone.

Compositions of the invention can also be used to lower homocysteine, restoring S-adenosylmethionine, reducing nuclear uracil, and/or preserving the methyl pool.

The exogenous ketone body as a source of acetyl Co-A can also be used to preserve NAD for use in PARP-directed DNA repair. The presence of exogenous ketone body, such as BHB, results in consumption of fewer NAD+ per acetyl-CoA produced. Metabolism of one molecule of glucose to two molecules of acetyl-CoA involves conversion of four molecules of NAD+ into NADH. Two of these are converted in the cytosol during glycolysis, and two in the mitochondrion by pyruvate decarboxylase. The cytosolic NADHs are shuttled into mitochondria, leading to depletion of the cytoplasmic NAD pool with high glucose utilization. By contrast, metabolism of one BHB molecule into the same two molecules of acetyl-CoA involves conversion of only two molecules of NAD+ into NADH, both in the mitochondrion by BDH1 and thereby preserving the cytoplasmic NAD pool. The cytoplasmic and mitochondrial NAD pools are relatively distinct; therefore, the preservation of cytoplasmic NAD+ by BHB may have important cellular effects. NAD+ is a cofactor for sirtuin deacylases (such as nuclear/cytoplasmic SIRT1) as well as poly-ADP-ribose polymerase (PARP). Consumption of NAD+ by PARP or overproduction of NADH may promote age-related diseases by inhibiting the activity of sirtuins. Conversely, repletion of NAD+ by exogenous feeding with nicotinamide mononucleotide has been shown to improve glucose tolerance in both high-fat diet-fed and aged mice. The relative sparing of NAD+ by utilization of BHB vis a vis glucose may therefore have important consequences for metabolic diseases and diabetes.

It has been shown that in some instances hypoxia results in increased PARP and DNA polymerase activity, for example, in cerebral cortical neuronal nuclei to repair the hypoxia-induced damage to genomic DNA. In addition, high-altitude illness is caused primarily by hypobaric hypoxia (HH), which is an acute physiological stressor that impacts the central nervous system, resulting in several physiological adaptations. In general, the severity and duration of the symptoms vary, depending on the altitude and rate of ascent, often persisting after returning to lower altitudes. The development of these symptoms has been linked to hypoxia-induced oxidative and nitrosative stress. HH promotes an increase in NO production, which correlates with PARP activation. Specifically, PARP-1 detects DNA-strand breaks caused by genotoxic agents, such as peroxynitrite and reactive oxygen species (ROS) associated with hypoxia. Hypoxia-inducible factor(s) (HIF-1 and HIF-2) are transcription factors with a central role in the accommodation of hypoxia. PARP-1 forms a physical complex with HIF-2, which promotes the expression of HIF-2 mediated genes. Thus, PARP-1 activation facilitates HIF-1 and HIF-2 activation, which subsequently contributes to the downregulation of mitochondrial activity. The downregulation of mitochondrial activity is concomitant with the depletion of NAD+, which is triggered by PARP assembly.

Obstructive sleep apnea (OSA) is associated with inter alia intermittent hypoxia, PARP activation, lower intraepidermal nerve fiber density (IENFD), peripheral neuropathy (DPN), and diabetic foot ulceration (DFU), which may occur in the presence of type 2 diabetes. The intermittent hypoxia of OSA may also occur in obese or non-obese states. PARP activation is a potential mechanism linking OSA to DPN and endothelial dysfunction in those with obesity, metabolic syndrome, or type 2 diabetes.

Compositions of the invention can also be used to reduce the adverse effects of PARP activation due to hypoxia or intermittent hypoxia by providing a non-glycogenic energy substrate, an NAD+ precursor (NR), and methyl donors. Thus, compositions of the invention can be used to prevent the ATP depletion associated with PARP activation without adversely affecting methyl donor pool (such as S-adenosylmethionine, betaine, choline, $B_{12}$, folate). Exemplary clinical conditions that can be treated by reducing/preventing ATP depletion associated with PARP activation include altitude-related hypobaric hypoxia, obstructive sleep apnea, endothelial dysfunction, lower intra-epidermal nerve density loss, diabetic peripheral neuropathy, and diabetic foot ulceration.

The amount of exogenous methyl donor, as vitamin B12 or folate, present in the composition of the invention can range from about 0.0001 mg to about 20 mg, typically from about 400 mcg to about 5 mg, and often from about 800 mcg to about 10 mg.

The amount of exogenous methyl donor, as betaine, present in the composition of the invention can range from about 0.001 mg to about 5,000 mg, typically from about 150 mg about 500 mg, and often from about 500 mg to about 1,500 mg.

The amount of exogenous methyl donor, as choline, present in the composition of the invention can range from about 0.001 mg to about 2,000 mg, typically from about 100 mg to about 400 mg, and often from about 25 mg to about 500 mg.

The amount of exogenous methyl donor, as S-adenosylmethionine, present in the composition of the invention can range from about 0.001 mg to about 2,000 mg, typically from about 100 mg to about 500 mg, and often from about 25 mg to about 500 mg.

In some embodiments, the compositions of the invention also include choline. Exemplary forms of choline that can be used in compositions of the invention include, but are not limited to, choline citrate (Citicholine), choline bitartrate, phosphatidylcholine, alpha-GPC (L-Alpha Glycerylphosphorylcholine), CDP choline (cytidine 5'-diphosphocholine) and the like.

Exemplary betaine that can be used in composition of the invention includes, but is not limited to, betaine monohydrate, betaine anhydrous, trimethylglycine (TMG) and the like.

Exemplary forms of vitamin $B_{12}$ that can be used in compositions of the invention include, but are not limited to, cyanocobalamin, methylcobalamin, hydroxocobalamin, adenosylcobalamin and the like.

Exemplary forms of folate that can be used in compositions of the invention include, but are not limited to, folinic acid, 5-methyltetrahydrofolate, L-methylfolate, L-methylfolate calcium and the like.

Exemplary forms of S-adenosylmethionine that can be used in compositions of the invention include, but are not limited to, S-adenosylmethionine.

In some embodiments, the ratio of the exogenous NAD modulator to the exogenous methyl donor in the composition of the invention ranges from about 5,000:1 to about 1:1, typically from about 500:1 to about 3:1 and often from about 1000:1 to about 2:1. In other embodiments, the ratio of the exogenous NAD modulator to the exogenous methyl donor as vitamin $B_{12}$ or folate ranges from about 6.25:1 to about 50,000,000:1, typically from about 25:1 to about 2500:1 and often from about 25:1 to about 1250:1. Still in other embodiments, the ratio of the exogenous NAD modulator to the exogenous methyl donor as betaine ranges from about 1:1 to about 5,000,000:1, typically from about 1.667:1 to about 6.667:1 and often from about 0.25:1 to about 1.333:1. Yet in other embodiments, the ratio of the exogenous NAD modulator to the exogenous methyl donor as choline ranges from about 1:1 to about 5,000,000:1, typically from about 2.5:1 to about 10:1 and often from about 5:1 to about 80:1. In other embodiments, the ratio of the exogenous NAD modulator to the exogenous methyl donor as S-adenosylmethionine ranges from about 1:1 to about 5,000,000:1, typically from about 0.625:1 to about 10:1 and often from about 5:1 to about 80:1.

Compositions of the invention can be used for other indications in addition to those disclosed above. In one embodiment, compositions of the invention can be used to increase the lifespan of a cell or a subject. Compositions of the invention can also be used in treating and/or preventing a wide variety of diseases and disorders including, for example, diseases or disorders related to aging or stress, diabetes (type I or type II), obesity, neurodegenerative diseases (such as Alzheimer's disease and neurocognitive impairment, etc.), cardiovascular disease, muscular disorders, blood clotting disorders, inflammation, cancer, eye disorders, or to promote alertness or improve cognitive function, to treat or improve hypoxic conditions, or to improve athletic performance, or to improve work capacity in an extreme environment or work condition.

Compositions of the invention can also be used to treat or prevent one or more of cataracts, retinopathy, retinitis pigmentosa, ocular neuritis or a vascular disease of the capillary beds of the eye.

In addition, compositions of the invention are useful in reducing the weight of a subject, preventing weight gain in a subject and/or increasing the ratio of lean muscle/fat ratio in a subject.

Compositions of the invention are also useful in preventing a subject from acquiring insulin insensitivity or treating or preventing insulin resistance disorders.

In some embodiments, compositions of the invention consist essentially of EK, NAD modulator, a methyl donor and optionally a pharmaceutically acceptable carrier or excipient.

As discussed above, compositions of the invention comprising EK, NAD modulator and a methyl donor can be used to reduce the adverse effects of PARP activation, such as preventing ATP depletion associated with PARP activation. Compositions of the invention are particularly useful in reducing the adverse effects of PARP activation due to the presence of a methyl donor. By including a methyl donor, compositions of the invention do not adversely affect in vivo (i.e., naturally occurring) methyl donor pool (such as S-adenosylmethionine, betaine, choline, $B_{12}$, folate), i.e., the natural amount of methyl donor is not depleted significantly (about 20% of less, typically about 10% of less, and often about 5% or less).

Specific examples of clinical conditions that can be treated by reducing/prevention ATP depletion associated with PARP activation using compositions of the invention include, but are not limited to, a neurodegenerative disease, stroke, Alzheimer's disease, dementia, cognitive impairment, Huntington's disease, Parkinson's disease, multiple sclerosis, diseases of myelin, mitochondrial disorders, muscle weakness, fatigue, depression, anxiety, age-related hearing loss, hypoxia, hyperoxia, altitude-related hypobaric hypoxia, obstructive sleep apnea, diabetes, endothelial dysfunction, lower intra-epidermal nerve density loss, peripheral neuropathy, diabetic foot ulceration, non-alcoholic fatty liver disease, traumatic brain injury, and epilepsy. This includes the effects of radiation associated with occupational exposure, military combat, terrorism, nuclear accidents, space flight, medical treatment, and others. Exemplary forms of radiation that trigger DNA damage and repair include, electromagnetic radiation, such as infrared, ultraviolet, radio waves, visible light, x-rays, and gamma radiation ($\gamma$); particle radiation, such as alpha radiation ($\alpha$), beta radiation ($\beta$), and neutron radiation (particles of non-zero rest energy); solar energetic particle radiation (energetic electrons, protons, alpha particles, and heavier particles); acoustic radiation, such as ultrasound, sound, blast waves, shock waves, and seismic waves (dependent on a physical transmission medium); gravitational radiation, radiation that takes the form of gravitational waves.

Compositions of the invention can also be used to prevent brain N-acetylaspartate (NAA) depletion associated with PARP activation without adversely affecting methyl donor pool (e.g., S-adenosylmethionine, betaine, choline, $B_{12}$, folate). Exemplary clinical conditions that can be treated by preventing NAA depletion associated with PARP activation include stroke, Alzheimer's disease, dementia, cognitive impairment, Huntington's disease, multiple sclerosis, diseases of myelin, mitochondrial disorders, muscle weakness, fatigue, depression, anxiety, age-related hearing loss, and epilepsy. Diminished NAA is considered a marker for neuronal injury, morbidity, or metabolic dysfunction. Traumatic brain injury (TBI) results in a reduction in brain NAA levels. NAA depletion is also noted in brain injury due to therapeutic radiation of brain tumors.

It should be noted that when the methyl donor pool is preserved by including a methyl donor in compositions of the invention, accumulation of uracil (U) in the nucleus is prevented or is significantly reduced. For example, if NAD modulator is used without a methyl donor, it will result in increased U concentration in the nucleus as reduction in the methyl donor prevents conversion of uracil (U) to thymine (T). Increase in uracil concentration in nucleus can lead to a wide variety of undesired side-effects including, but not limited to, single or double strand breaks in DNA, and reduced ability of cells to repair DNA damage even with PARP activation. By providing a methyl donor, use of compositions of the invention preserves thymine synthesis, DNA stability, and the further potentially adverse effect on needing DNA repair enzymes, such as uracil glycosylases.

Compositions of the invention comprising EK, NAD modulator and a methyl donor can also be used to reduce the adverse effects of PARP activation, such as dysregulated ATP metabolism, lactate metabolism, and aberrant cell growth without adversely affecting methyl donor pool (such as S-adenosylmethionine, betaine, choline, vitamin $B_{12}$, folate). Exemplary clinical conditions that can be treated by reducing/prevention ATP and lactate dysregulation associated with PARP activation include cancer. Glucose is a substrate for cancer cell biomass via glycolysis and conversion to lactate. Tumor cells cannot metabolize ketone bodies readily. Therefore, by providing ketone bodies as a fuel for cancer therapy and restricting glucose consumption, compositions of the invention can also be used to treat cancer.

In some embodiments, the presence of EK protects against ionizing radiation. Accordingly, compositions of the invention can also be used in treating cancer, reducing the side-effects of chemotherapy and/or radiotherapy.

Without being bound by any theory, it is believed that compositions of the invention also increase the number of cellular mitochondria in a subject. This increase results in higher energy expenditure resulting in weight loss and/or decrease in the total amount of fat in a subject. Accordingly, in some embodiments, compositions of the invention are useful in preservation, restoration, or resynthesis of glycogen. In other embodiments, compositions of the invention are useful in increasing performance and endurance such as in athletics and other stressful situations such as in combats.

In general, the compositions of the invention are administered in a therapeutically effective amount by any of the accepted modes of administration for agents that serve similar utilities. Generally, compositions of the invention are administered as nutraceutical or pharmaceutical formulations including those suitable for oral (including buccal and sub-lingual), administration. Typical manner of administration is generally oral using a convenient daily dosage regimen.

Compositions of the invention, together with one or more conventional adjuvants, carriers, or diluents, can be placed into unit dosages. The compositions and unit dosage forms can be comprised of conventional ingredients in conventional proportions, with or without additional nutraceutical compounds or principles. The compositions of the invention can be employed as solids, such as tablets or filled capsules, semisolids, powders, sustained release formulations, or liquids such as solutions, suspensions, emulsions, elixirs, or filled capsules for oral use.

The compositions of the invention can be formulated in a wide variety of oral administration dosage forms. The compositions and dosage forms can comprise one or more nutraceutically acceptable carriers and can be either solid or liquid. Solid form preparations include powders, tablets, pills, capsules, cachets, and dispersible granules. A solid carrier can be one or more substances which can also act as diluents, flavoring agents, solubilizers, lubricants, suspending agents, binders, preservatives, tablet disintegrating agents, or an encapsulating material. In powders, the carrier generally is a finely divided solid mixture which includes a finely divided active component. In tablets, the compositions of the invention generally are mixed with the carrier having the necessary binding capacity in suitable proportions and compacted in the shape and size desired.

It should be appreciated other nutrients such as vitamins, mineral including trace minerals can also be included in compositions of the invention.

When formulated as a unit dosage form, compositions of the invention can also include one or more suitable carriers. Suitable carrier include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" or "unit dosage" is intended to include the formulation of the compositions of the invention with encapsulating material as carrier, providing a capsule in which the compositions of the invention, with or without carriers, is surrounded by a carrier, which is in association with it. Similarly, cachets and lozenges are included. Tablets, powders, capsules, pills, cachets, and lozenges can be as solid forms suitable for oral administration.

Other forms suitable for oral administration include liquid form preparations including emulsions, syrups, aqueous solutions, aqueous suspensions, or solid form preparations which are intended to be converted shortly before use to liquid form preparations. Emulsions can be prepared in solutions, for example, in aqueous propylene glycol solutions or may contain emulsifying agents, for example, such as lecithin, sorbitan monooleate, or acacia. Aqueous solutions can be prepared by dissolving the compositions of the invention in water and adding suitable colorants, flavors, stabilizers, and thickening agents. Aqueous suspensions can be prepared by dispersing the finely divided compositions of the invention in water with viscous material, such as natural or synthetic gums, resins, methylcellulose, sodium carboxymethylcellulose, and other well-known suspending agents. Solid form preparations include solutions, suspensions, and emulsions, and can contain, in addition to the compositions of the invention, colorants, flavors, stabilizers, buffers, artificial and natural sweeteners, dispersants, thickeners, solubilizing agents, and the like.

The nutraceutical preparations are typically in unit dosage forms. In such form, the preparation is often subdivided into unit doses containing appropriate quantities of the active component (e.g., exogenous ketone body, exogenous NAD modulator and methyl donor). The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

When it is possible that, for use in therapy, therapeutically effective amounts of a composition of the invention, as well as pharmaceutically acceptable salts thereof, can be administered as the raw chemical, it is possible to present the active ingredient (i.e., exogenous ketone body, exogenous NAD modulator and methyl donor) as a nutraceutical or pharmaceutical composition. Accordingly, the disclosure further provides nutraceutical and/or pharmaceutical compositions, which include therapeutically effective mounts of active ingredients (i.e., exogenous ketone body, exogenous NAD modulator and in some embodiments optionally present methyl donor), and one or more nutraceutically or pharmaceutically acceptable carriers, diluents, or excipients. When applied to a combination, the term refers to combined amounts of the active ingredients that result in the therapeutic effect, whether administered in combination, serially, or simultaneously. The carrier(s), diluent(s), or excipient(s) must be acceptable in the sense of being compatible with the other ingredients of the formulation and not deleterious to the recipient thereof. In accordance with another aspect of the disclosure there is also provided a process for the preparation of a nutraceutical or pharmaceutical formulation including admixing the active ingredients with one or more nutraceutically or pharmaceutically acceptable carriers, diluents, or excipients.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

The mixture of exogenous NAD modulator, exogenous ketone, and exogenous methyl donor(s) are incorporated into an oral dosage formulation including, but not limited to, a stabilized gel, liquid formulation, and/or bulk powder; which may or may not be incorporated into a food matrix, with a unit dosage set within the range set forth herein. The unit dosage form is incorporated with the appropriate excipients as needed, which is dictated by the set formulation.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All references cited herein are incorporated by reference in their entirety.

I claim:

1. A composition comprising a therapeutically effective amount of:
    (i) an exogenous ketone body present in the composition in an amount from 1 mg to 50,000 mg, wherein the exogenous ketone body comprises 3-hydroxybutyrate ("BHB") or an ester of BHB;
    (ii) an exogenous nicotinamide adenine dinucleotide ("NAD") modulator; and
    (iii) a methyl donor;
    wherein the ratio (w/w) of the exogenous ketone body to the exogenous NAD modulator is from 160:1 to 10:1; and
    wherein the composition is in a single unit form.

2. The composition of claim 1, wherein the methyl donor is selected from the group consisting of choline, betaine, folate, vitamin B12, or S-adenosylmethionine.

3. The composition of claim 2, wherein the methyl donor is betaine.

4. The composition of claim 3, wherein the betaine is present in the composition in an amount from 0.001 mg to 5,000 mg.

5. The composition of claim 4, wherein the betaine is present in the composition in an amount from 150 mg to 1500 mg.

6. The composition of claim 3, wherein the ratio (w/w) of the exogenous NAD modulator to betaine ranges from 0.25:1 to 6.667:1.

7. The composition of claim 2, wherein the exogenous ketone body comprises BHB.

8. The composition of claim 2, wherein the exogenous ketone body comprises an ester of BHB.

9. The composition of claim 8, wherein the ester of BHB is of the formula:

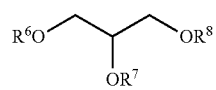

G-1 wherein
    each of $R^6$, $R^7$, and $R^8$ is independently selected from the group consisting of hydrogen, BHB moiety or an acyl group;
provided at least one of $R^6$, $R^7$, and $R^8$ is BHB moiety of the formula —C(=O)CH$_2$CH(OR$^2$)CH$_3$, wherein $R^2$ is H or a hydroxyl protecting group.

10. The composition of claim 2, wherein the exogenous NAD modulator is nicotinoyl riboside, nicotinamide riboside, nicotinic acid mononucleotide, nicotinamide mononucleotide, ß-nicotinamide ribose monophosphate, or a combination thereof.

11. The composition of claim 10, wherein the exogenous NAD modulator is nicotinamide riboside, and wherein the nicotinamide riboside comprises a protecting group comprising an acetyl group (CH3C(=O)—), an acetoacetyl group, formate, benzoate, or carbamate.

12. The composition of claim 2, wherein the exogenous NAD modulator is present in the composition in an amount from 0.001 mg to 5,000 mg.

13. The composition of claim 2, wherein the exogenous NAD modulator is present in the composition in an amount from 125 mg to 2000 mg.

14. The composition of claim 2, wherein the ratio (w/w) of exogenous NAD modulator to methyl donor is between 0.25:1 to 6.667:1.

15. The composition of claim 1, further comprising a carrier.

16. The composition of claim 15, wherein the carrier is a liquid.

17. The composition of claim 15, wherein the composition is an emulsion, syrup, aqueous solution, or aqueous suspension.

18. The composition of claim 15, wherein the carrier comprises one or more of propylene glycol, lecithin, sorbitan monooleate, acacia, thickening agents, natural or synthetic gums, resins, methylcellulose, flavors, sweeteners, colorants, or sodium carboxymethylcellulose.

19. The composition of claim 15, wherein the composition is a solid.

20. The composition of claim 19, wherein the composition is formulated as a powder, tablet, pill, capsule, cachet, lozenge, or as dispersible granules.

21. The composition of claim 19, wherein the composition comprises one or more of a diluent, flavoring agent, solubilizer, lubricant, suspending agent, binder, preservative, tablet disintegrating agent, or encapsulating material.

22. The composition of claim 9, wherein:
the exogenous NAD modulator is nicotinoyl riboside, nicotinamide riboside, nicotinic acid mononucleotide, nicotinamide mononucleotide, ß-nicotinamide ribose monophosphate, or a combination thereof, wherein the exogenous NAD modulator is present in the composition in an amount from 0.001 mg to 5,000 mg; and
wherein the methyl donor is betaine, wherein betaine is present in the composition in an amount from 0.001 mg to 5,000 mg.

23. The composition of claim 22, wherein betaine is present in the composition in an amount from 150 mg to 1500 mg.

24. The composition of claim 23, wherein the ratio (w/w) of the exogenous NAD modulator to betaine ranges from 0.25:1 to 6.667:1.

25. The composition of claim 1, wherein the exogenous ketone body is BHB, and the BHB is in its free acid form.

* * * * *